United States Patent [19]

Rasmussen

[11] 4,182,865

[45] Jan. 8, 1980

[54] DIAZA-CYCLIC DERIVATIVES OF GUANIDINE

[75] Inventor: Chris R. Rasmussen, Ambler, Pa.

[73] Assignee: McNeil Laboratories, Inc., Fort Washington, Pa.

[21] Appl. No.: 943,098

[22] Filed: Sep. 18, 1978

[51] Int. Cl.$^2$ .................. C07D 413/02; C07D 233/48
[52] U.S. Cl. ........................................ 544/60; 544/62; 544/139; 544/370; 546/197; 546/203; 546/205; 546/210; 548/315; 548/316
[58] Field of Search ................... 544/139, 370, 60, 62; 548/315, 316; 546/197, 210, 203, 205

[56] References Cited

U.S. PATENT DOCUMENTS

| 3,479,437 | 11/1969 | Szabo et al. | 424/326 |
| 3,669,974 | 6/1972 | Elpern et al. | 424/326 |

FOREIGN PATENT DOCUMENTS 1409768  10/1975  United Kingdom ..................... 548/315

*Primary Examiner*—Alan L. Rotman
*Assistant Examiner*—R. W. Ramsuer

[57] ABSTRACT

5-Membered 1,3-diazacarbocyclic derivatives of guanidine having hypoglycemic activity.

8 Claims, No Drawings

DIAZA-CYCLIC DERIVATIVES OF GUANIDINE

BACKGROUND OF THE INVENTION

In British Pat. No. 1,409,768 there are described several heterocyclic derivatives of guanidine in which the heterocyclic moiety is a 5- or 6-membered saturated 1,3-diazacarbocyclic-2-ylidene. These derivatives are unsubstituted on the imino nitrogen of the guanidine moiety. In contrast, the compounds of the present invention differ by being a di-aza heterocyclic derivative of guanidine which carries a bulky substituent on the imino nitrogen of the guanidine moiety. Additional prior art, but further related, may be represented by German Offen. Nos. 2,321,330 and 2,502,397; U.S. Pat. Nos. 3,914,306, 3,933,836 and 4,073,636; and British Pat. No. 1,341,245.

DESCRIPTION OF THE PREFERRED EMBODIMENTS

This invention relates to new heterocyclic derivatives of guanidine having interesting pharmacological properties and, more particularly, to such derivatives having the formula:

$$Z-C(=NR_3)-N(R_1)(R_2) \quad (I)$$

wherein:

Z is a member selected from the group consisting of:

(a) [N,N'-dimethyl-imidazolin-2-ylidene]-NH (Tautomeric form with =N and NH-Me)

(b) [N,N'-dimethyl-imidazolin-2-ylidene]=N, and (c) [N-methyl-tetrahydropyrimidin-2-ylidene]-NH $R_1$ is a member selected from the group consisting of methyl and ethyl;

$R_2$ is a member selected from the group consisting of loweralkyl (preferably methyl and ethyl), cycloalkyl having from 3 to 6 carbons (preferably cyclopentyl and cyclohexyl) and aralkyl (preferably benzyl);

$$-N(R_1)(R_2)$$

taken together represents a member selected from the group consisting of:

-N(pyrrolidinyl), -N(piperidinyl), and -N(piperazinyl)-W, wherein W is a member selected from the group consisting of O, S, N-loweralkyl (preferably N-methyl) and N-aryl (preferably N-phenyl); and $R_3$ is a member selected from the group consisting of:

- alkyl having from 4 to 10 carbons (preferably branched), such as, for example, tert-butyl, neopentyl, 1,1,3,3-tetramethylbutyl (tert-octyl) and the like;
- phenyl; methylenedioxyphenyl; phenyl substituted with from 1 to 3 substituents each selected from the group consisting of halo, loweralkyl and loweralkoxy; and phenyl substituted with a member selected from the group consisting of hydroxy, benzyloxy, nitro; trifluoromethyl and methylthio;
- naphthyl;
- cycloalkyl having from 5 to 8 carbons (preferably cyclopentyl and cyclohexyl);
- bicycloalkyl having from 7 to 10 carbons, such as, for example, exo- and endo-2-norbornyl, 2-bicyclo[2.2.2.]octyl, endo-2-bicyclo[3.2.1.]octyl and the like;
- tricycloalkyl having from 9 to 10 carbons, such as, for example, nor-adamantyl, 1- and 2-adamantyl, 1- and 2-(2,3,3a,4,5,6,7,7a-octahydro-4,7-methanoindenyl) and the like;
- arylalkyl in which the aryl function is a member selected from the group consisting of phenyl and naphthyl and the akyl function has from 1 to 4 carbons, such as, for example, benzyl, dl-, d- or l-α-phenethyl, dl, d- or l-α-methylbenzyl, α,α-dimethylbenzyl, α,α-dimethyl-β-phenethyl, dl, d- or l-(α-naphthyl)ethyl and the like; and
- diphenylalkyl in which the alkyl function has from 1 to 2 carbons, such as, for example, diphenylmethyl, 1,2- and 2,2-diphenylethyl and the like.

As used herein, the prefix "lower" indicates that the relevant group has 1 to 4 carbons and the term "halo" represents halogens of atomic weight less than 127, i.e., chloro, bromo, fluoro, and iodo.

Due to the presence of amine-like nitrogen atoms in the compounds of formula (I), acid addition salts thereof are readily obtained and such pharmaceutically acceptable salts are included within the scope of this invention. The subject compounds (I) may be converted to their therapeutically active nontoxic acid addition salt form by treatment with an appropriate acid, such as, for example, an inorganic acid, such as hydrohalic acid, e.g., hydrochloric, hydrobromic and the like, and sulfuric acid, nitric acid, phosphoric acid and the like, or an organic acid, such as, for example, acetic, propionic, glycolic, pamoic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids. Conversely, the salt form can be converted by treatment with alkali into the free base form.

The subject compounds of formula (I) may be prepared from the starting materials of formula (II), wherein Z is as previously described. Said starting materials (ZH) may be reacted with an isothiocyanate of formula (III), wherein $R_3$ is as previously described other than hydroxyphenyl, in a reaction-inert organic solvent, e.g., benzene, $CH_2Cl_2$, chloroform and the like at temperatures ranging from about ambient to reflux temperatures, for about 2 to 24 hrs, in approximately equimolar amounts. The thio function (=S) in the thus-obtained thioureas (IV), is then transformed into an alkylthio function (—SR′) by reacting (IV) with an alkylating agent of the formula R′X, wherein R′ is ethyl or, preferably, methyl, and X is halide, preferably iodide, tosylate, methosulfate, mesylate, fluorosulfonate and the like, Typical solvents for such alkylations include ethers, preferably diethyl ether, tetrahydrofuran, or dioxane, lower ketones, e.g., acetone, 2-butanone and the like; halohydrocarbons and loweralkanols, preferably methylene dichloride and methanol, respectively. Methyl iodide as the alkylating agent in methanol is particularly suitable. Generally, equimolar to a large stoichiometric excess of the alkylating agent is used, the amount depending on the reactivity of the thiourea (IV) or its solubility in the solvent employed. The alkylation reaction may be carried out at temperatures ranging from ambient to reflux or in appropriate sealed vessels at higher temperatures. The alkylthio compounds of formula (V) in acid addition (HX) salt form are then reacted with an appropriate amine of the formula $HNR_1R_2$, wherein $R_1$, $R_2$ and $NR_1R_2$ are as previously described, preferably in a lower alkanol solvent such as isopropanol and tert-butanol and generally at reflux temperatures of about 40°–100° C., to yield the guanidine derivatives of formula (I), in similar acid addition form, which are readily obtained as the corresponding base form by conventional treatment with suitable alkali. The foregoing reactions may be illustrated as follows:

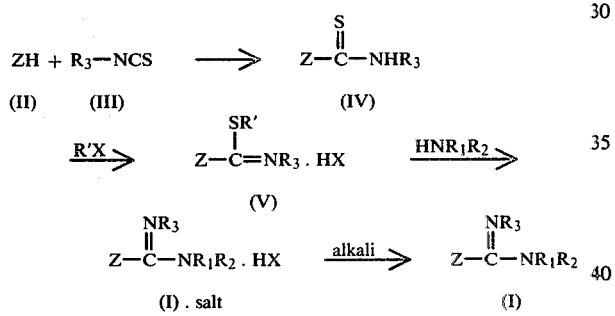

The isothiocyanates of formula (III), many of which are known, may be prepared according to the extensive processes reported in the literature for making isothiocyanates. For example, they may be obtained from the methodologies reported by M. Bögemann et al. in "Methoden der Organische Chemie Houben-Weyl", Eugen Müller (Ed.), Georg Thieme Verlag (Publ.) Stuttgart, Germany, Vol. 9, page 867–884 (1955); "Preparation des Isothiocyanates Aromatiques" by A. Rasschaert et al., Ind. Chim., Belge, 32, 106 (1967); German Pat. No. 1,300,559; J. Org. Chem., 36, 1549 (1971); U.S. Pat. Nos. 2,395,455 and 3,304,167; French Pat. No. 1,528,249; "A New Synthesis of Aliphatic Isothiocyanates", Angew. Chem. internat. Ed., 6, 174 (1967); Bull. Chem. Soc. Japan, 48, 2981 (1975); Tetrahedron, 29, 691 (1973); Chem. Ber., 101, 1746 (1968); and J. Indian Chem. Soc., 52, 148 (1975).

In the foregoing reaction of (V) with the amine, $HNR_1R_2$, it is preferred to use a stoichiometric excess of the latter, for example, in 1:1.05 to 1:2.0 molar ratios. If only a slight excess of the $HNR_1R_2$ amine is used, it may be advantageous to add a stoichiometric equivalent of a tertiary alkyl amine, e.g., $Et_3N$, in order to enhance the rate of reaction. Any by-products which may be formed during the course of the reaction can be separated from the desired formula (I) product by standard techniques known in the art, such as, for example, by fractional solubilization.

The compounds of formula (I), wherein $R_1$, $R_2$, $NR_1R_2$ and $R_3$ (other than hydroxyphenyl) are as previously defined and Z is equal to the diaza function represented by letter (b), are alternatively prepared by reacting a pseudouronium salt of formula (VI), wherein X is either methoxy or ethoxy and $Y^\ominus$ is either $BF_4^\ominus$ or $OSO_2F^\ominus$, with a guanidine derivative of formula (VII), with stoichiometric quantities of reactants being preferably employed. The preparation of said guanidine derivatives (VII) is described in my copending application Ser. No. 828,561, filed Aug. 29, 1977, and entitled "Heterocyclic Derivatives of Guanidine". It is often advantageous to add four to eight molar equivalents of potassium carbonate to the reaction mixture following addition of the guanidine (VII) in order to cause the reaction to proceed toward completion. Suitable anhydrous organic solvents for conducting the reaction include lower aliphatic alcohols, such as, for example, methanol, ethanol, 2-propanol, tert-butanol and the like; ethers, such as, for example, diethylether, tetrahydrofuran, dioxane and the like; and lower halogenated hydrocarbons, such as, for example, chloroform, methylene chloride, 1,2-dichloroethane and the like. Generally, methylene chloride is preferred. Ambient to 0° C. temperatures may generally be employed. The product (VIII), in the form of the corresponding HY salt, is converted to the corresponding base form (I) by conventional means, for example, by treatment with a suitable alkali such as alkali metal or alkaline earth metal hydroxides; carbonates and the like. The reaction may be illustrated as follows:

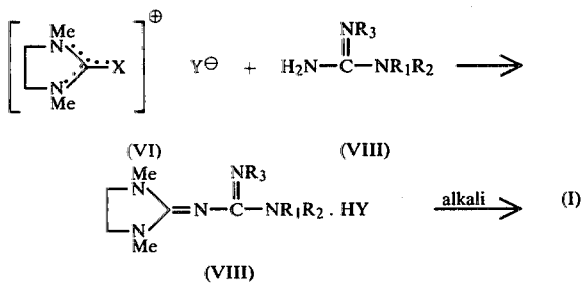

The pseudouronium fluoborates of formula (VI), wherein $Y^\ominus$ is $BF_4^\ominus$, may be obtained according to procedures described in the literature, e.g., see Canadian Pat. Nos. 850,116 and 950,464; U.S. Pat. No. 3,876,658; Ber. 89, 2063 (1956); and Org. Synth. 46, 113, 120 (1966). The pseudouronium fluorosulfonates of formula (VI), wherein $Y^\ominus$ is $OSO_2F^\ominus$, are similarly prepared. In general, a cyclic urea of formula (IX) is reacted with an appropriate trialkyl oxonium fluoborate (X) or methyl fluorosulfonate (XI) to give the corresponding salt (VI). The reaction is preferably carried out from 0° C. to ambient temperature under an inert dry atmosphere (e.g., nitrogen, argon) in an inert anhydrous lower halohydrocarbon solvent such as, for example, chloroform, 1,2-dichloroethane, methylene dichloride (most preferred) and the like. Other inert anhydrous organic solvents that may be employed include ethers such as, for example, diethyl ether, dioxane, tetrahydrofuran (THF), 1,2-dimethoxyethane and the like. The foregoing reactions may be illustrated as follows:

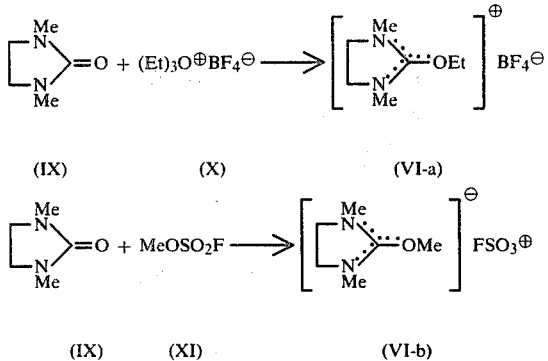

(IX)    (X)    (VI-a)

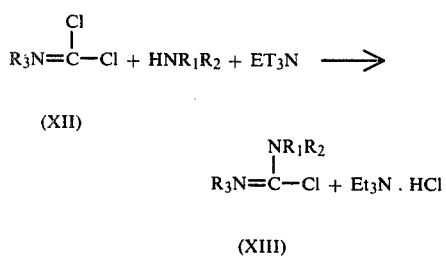

(IX)    (XI)    (VI-b)

Another method of preparing the formula (I) compounds utilizes the methodology described by E. Kuhle, Angew. Chem. internat. Ed., 8, 24, 26, (1969) and references cited therein, which involves the sequential displacement of chloride from an appropriate isocyanide dichloride (XII) wherein $R_3$ is other than hydroxyphenyl. The latter, the preparation of which is described by E. Kuhle et al. in Angew. Chem. internat. Ed., 6, 649 (1967), is reacted with the amine, $HNR_1R_2$, in the presence of a trialkylamine, e.g., triethylamine, in a suitable reaction-inert aprotic anhydrous solvent such as an ether, for example, diethyl ether, tetrahydrofuran and the like, a halohydrocarbon, an aromatic hydrocarbon, and the like, to give the monochloride compound (XIII) which is separated from triethylamine hydrochloride, by filtration, and then used in situ as the filtrate in the reaction with ZH (II) to form final product (I).

$$R_3N=\overset{Cl}{\underset{|}{C}}-Cl + HNR_1R_2 + ET_3N \longrightarrow$$

(XII)

$$R_3N=\overset{NR_1R_2}{\underset{|}{C}}-Cl + Et_3N \cdot HCl \downarrow$$

(XIII)

Preferably, two molar equivalents of ZH (II) are then reacted with each molar equivalent of (XIII). Alternatively, when Z is equal to the diaza function represented by letter (c), a 1:1 molar equivalent ratio of reactants may be employed in which case a molar equivalent of an appropriate halogen acid scavenger, for example, a base such as triethylamine, is added to pick up the hydrochloric acid released during the course of the reaction. In either route, the resultant precipitated acid addition salt is removed from the reaction mixture, e.g., by filtration, and the desired product (I) which remains in situ in the filtrate, is conveniently isolated by conversion to an acid addition salt in the conventional manner.

a.
$$2\ ZH + Cl-\overset{NR_3}{\underset{||}{C}}-NR_1R_2 \longrightarrow$$

(II)    (XIII)

$$Z-\overset{NR_3}{\underset{||}{C}}-NR_1R_2 + ZH \cdot HCl \ \downarrow$$

(I)

b.
$$ZH + Cl-\overset{NR_3}{\underset{||}{C}}-NR_1R_2 + Et_3N \longrightarrow$$

(II)    (XIII)

(I) + $Et_3N \cdot HCl$ 

Still another method of preparing the formula (I) compounds utilizes the methodology of H. G. Viehe and Z. Janousek, Angew. Chem. internat. Ed., 12(10), 806 (1973), from the interaction of an appropriate dichloromethyleneammonium salt of formula (XIV) with an equivalent amount of an appropriate amine of formula (XV), wherein $R_3$ is other than hydroxyphenyl, in the presence of at least two equivalents of an appropriate acid scavenger, e.g., triethylamine, to yield the aforementioned product (XIII) which may then be reacted with ZH (II) to form end products (I) as previously described.

$$R_3NH_2 + Cl-\overset{Cl}{\underset{|}{C}}=NR_1R_2^{\oplus}Cl^{\ominus} + 2\ Et_3N \longrightarrow$$

(XV)    (XIV)

$$Cl-\overset{NR_3}{\underset{||}{C}}-NR_1R_2 + 2\ Et_3N \cdot HCl \ \downarrow$$

(XIII)

In each of the foregoing synthetic procedures for preparing formula (I) compounds, hydroxyphenyl was excluded from the original definition of $R_3$. The formula (I) compounds wherein $R_3$ is hydroxyphenyl may be prepared either (i) be debenzylation of the corresponding $R_3$=benzyloxyphenyl derivatives by conventional procedures, e.g., by reduction via hydrogenation in the presence of palladium-on-carbon catalyst or (ii) by hydrolysis of the corresponding $R_3$=benzyloxyphenyl and methoxyphenyl derivatives by conventional procedures, e.g., by treatment with HBr or HI in acetic acid. This latter procedure is preferred when sulfur is present in the molecule, e.g., wherein $NR_1R_2=$

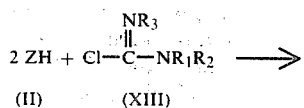

(thiamorpholine).

It is known that sulfur, when present in organic molecules in the divalent state, has a poisoning effect on hydrogenation catalysts, e.g., palladium-on-charcoal. Therefore it is preferred that compounds of formula (I) wherein $NR_1R_2$=thiamorpholine and $R_3$=hydroxyphenyl, be prepared by hydrolysis of either a corresponding $R_3$=methoxy-Ph or $R_3$=benzyloxy-Ph derivatives of formula (I) by the action of either HBr or HI in acetic acid.

The subject compounds of formula (I) and the acid addition salts thereof possess valuable pharmacological properties, particularly as hypoglycemic agents. Their ability to lower blood sugar is demonstrated in the following rat glucose tolerance test, which test is a standard and extremely sensitive procedure used in the diagnosis of diabetes and hypoglycemic disease states.

In this test, male Sprague-Dawley rats (Charles River 184–250 grams) are given water ad libitum and fasted 24 hours prior to the experiment. Two to five rats are used for each test and control group. Test compounds, 1–200 mg./kg., are administered (s.c., i.p. or orally) suspended in 0.5 or 1.0 milliliter, but preferably the former, of 0.5–1.0% methylcellulose vehicle. Control animals are given an equal amount of vehicle. Serial blood samples (0.1 milliliter) are obtained from the tail without anesthesia prior to and at 30, 60, 90, 120, 150 and 180 minutes after administration of 0.8 to 1.0 gram of glucose per kilogram of body weight in 1 milliliter of water. (The glucose is given orally if the test compound has been given parenterally, and subcutaneously if the test compound has been given orally.) Specimens of blood are immediately deproteinized with aqueous solutions of Ba(OH)$_2$ and ZnSO$_4$ and glucose levels are determined using the glucose oxidase assay described by L. P. Cawley et al., "Ultra Micro Chemical Analysis of Blood Glucose with Glucose Oxidase", Amer. J. Clin. Path., 32, 195 (1959). The blood glucose values at each time point at expressed in terms of milligram percent (mg glucose/100 ml of blood). The mean glucose values of the controls are compared statistically by the Student's t-Test to the means of the experimental group at each of the corresponding time points. If the compound lowers the blood glucose significantly at any time at a 95% confidence limit, the compound is considered to have hypoglycemic activity. The blood glucose lowering, expressed as percent lowering, is obtained by dividing the difference between the mean blood glucose values for test and control animals by the mean glucose value for the control animal.

In addition to their hypoglycemic activity, certain of the subject compounds have been found to possess antisecretory activity and/or cardiovascular activity as demonstrated in tests described in my copending patent application Ser. No. 828,561, filed Aug. 29, 1977, and entitled "Heterocyclic Derivatives of Guanidine".

The subject compounds (I), in base or salt form, may be formulated into conventional liquid and solid pharmaceutical dosage forms and preparations, for example, for oral or parenteral administration, according to standard pharmaceutical techniques in the art.

The following examples are intended to illustrate, but not to limit, the scope of the present invention. Unless otherwise stated, all parts are by weight.

EXAMPLE I

N-(1-methyl-2-imidazolidinylidene)-N'-phenylthiourea

2-Amino-1-methylimidazoline hydroiodide (26.75 g, 0.117 mole) is converted to its free base form by treatment with 50% sodium hydroxide. The base is extracted with methylene chloride and the extract dried over potassium carbonate and filtered. To this solution is added phenylisothiocyanate (15.81 g, 0.117 mole) and the reaction mixture is refluxed for three hours. The hot solution is filtered, concentrated to a small volume in vacuo, ether added, chilled, and the solid filtered off to give 23.6 g (86.1%) of N-(1-methyl-2-imidazolidinylidene)-N'-phenylthiourea; m.p. 205°–208° C.

EXAMPLE II

Methyl N-(1-methyl-2-imidazolidinylidene)-N'-phenylcarbamimidothioate hydroiodide A mixture of 22.0 g (0.094 mole) of N-(1-methyl-2-imidazolidinylidene)-N'-phenylthiourea and 14.9 g (0.105 mole) of methyliodide in 500 ml of acetone is refluxed for 2.5 hours. The reaction mixture is evaporated in vacuo and the oil obtained is crystallized from acetone-ether (1:1) to give 30 g (85%) of methyl N-(1-methyl-2-imidazolidinylidene)-N'-phenylcarbamimidothioate hydroiodide; m.p. 122°–126° C.

EXAMPLE III

The procedures of Examples I and II are followed except that an equivalent amount each of the appropriate reactants of formula (II) and of formula (III) are initially employed to prepare the desired thiourea of formula (IV), which is then treated with an appropriate S-methylating agent to yield as final products the indicated salt of the listed pseudothioureas of formula (V):

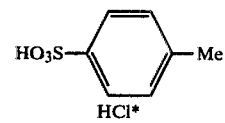

| No. | Z | R$_3$ | HX |
|---|---|---|---|
| 1 | (c) | 4-F-2-Me—Ph | HO$_3$SMe |
| 2 | (a) | 3-CF$_3$—Ph | HO$_3$S—⟨⟩—Me |
| 3 | (b) | 3-Br—Ph | HCl* |
| 4 | (c) | 3,4-diCl—Ph | HI |
| 5 | (b) | 2,3,4-triCl—Ph | HO$_3$SF |
| 6 | (c) | 5-Cl-2,4-diOMe—Ph | HI |
| 7 | (a) | 4-Br-2-Cl—Ph | HO$_3$SMe |
| 8 | (a) | 4-I—Ph | HI |
| 9 | (c) | 4-OEt—Ph | HI |
| 10 | (a) | 4-OMe-2-Me—Ph | HI |
| 11 | (b) | 3,4,5-triOMe—Ph | HI |
| 12 | (c) | 4-OBz—Ph | HI |
| 13 | (a) | 2-Et-6-Me—Ph | HI |
| 14 | (c) | 2,4,5-triMe—Ph | HI |
| 15 | (b) | 4-n-Bu—Ph | HI |
| 16 | (a) | 4-NO$_2$—Ph | HBr* |
| 17 | (a) | diphenylmethyl | HI |
| 18 | (c) | d,l-α-Me—Bz | HI |
| 19 | (a) | α,α-diMe-phenethyl | HI |
| 20 | (c) | 1,2-diphenethyl | HI |
| 21 | (a) | 1-adamantyl | HI |
| 22 | (c) | cyclohexyl | HI |
| 23 | (a) | endo-2-norbornyl | HI |
| 24 | (c) | tert-butyl | HI |
| 25 | (a) | tert-octyl | HI |
| 26 | (b) | 3,4-methylenedioxy-Ph | HI |
| 27 | (b) | Ph | HI |
| 28 | (a) | 4-OBz—Ph | HI |

*When MeBr and MeCl are used as the S-methylating agent, the reaction is preferably run in a sealed vessel.

[Note: Me = methyl; Et = ethyl; Bu = butyl; Ph = phenyl and Bz = benzyl.]

EXAMPLE IV

N-(1-methyl-2-imidazolidinylidene)-N'-phenyl-1-pyrrolidinecarboximidamide fumarate A mixture of 10.0 g (0.042 mole) of methyl N-(1-methyl-2-imidazolidinylidene)-N'-phenylcarbamimidothioate hydroiodide and 6.4 g (0.090 mole) of pyrrolidine in 200 ml of t-butanol is refluxed overnight (about 16 hours) under a slow stream of nitrogen. Sodium hypochlorite and NaOH traps are used to remove the methyl mercaptan formed in the reaction. The reaction mixture is cooled, ether is added, and the formed solid is filtered to yield 11.4 g (67%) of hydroiodide salt; m.p. 237°–240° C. The conversion to the free base is done by partitioning the hydroiodide between 3 N sodium hydroxide and methylene chloride. The organic layer is dried over potassium carbonate, filtered and evaporated in vacuo to give 7.6 g (0.028 mole) of free base, which is converted to the fumarate salt with an equimolar amount of fumaric acid in 2-propanol. Two recrystallizations from ethanol-ether gives 7.5 g (68%) of pure product, N-(1-methyl-2-imidazolidinylidene)-N'-phenyl-1-pyrrolidinecarboximidamide fumarate, m.p. 163°–165° C.

EXAMPLE V

By following the procedure of Example IV, except that an equivalent amount of each pseudothiouronium salt in Example III is reacted with an equivalent amount of an appropriate amine (HNR₁R₂), there are obtained as final products, with or without conversion to the indicated acid addition salt, the following compounds of formula (I). In the table, the compound number corresponds to the compound number in the table of Example III.

| No. | —NR₁R₂ | Hx |
|-----|--------|-----|
| 1 | —N(Me)—[thiolane] | HO₃SMe |
| 2 | —N[morpholine] | HO₃S—C₆H₄—Me |
| 3 | —N[pyrrolidine] | HCl |
| 4 | —N(Me)—[thiane] | HI |
| 5 | —N[piperidine] | maleate |
| 6 | —N[piperazine]N—Ph | 2 HI |
| 7 | —NEt₂ | HO₃SMe |
| 8 | —N[morpholine] | HI |
| 9 | —N[piperazine]N—Ph | 2 HI |
| 10 | —N(Me)Bz | HI |
| 11 | —N[piperidine] | HI |
| 12 | —N[thiomorpholine] | HI |
| 13 | —NEt₂ | fumarate |
| 14 | —N[pyrrolidine] | succinate |
| 15 | —N[morpholine] | HI |
| 16 | —N[thiomorpholine] | HBr |
| 17 | —N[piperidine] | HI |
| 18 | —N[piperazine]N—Me | 2 HI |
| 19 | —NMe₂ | HI |
| 20 | —N[pyrrolidine] | HI |
| 21 | —NEt₂ | HI |
| 22 | —N(Me)[thiolane] | HI |
| 23 | —N[morpholine] | HI |
| 24 | —N[thiomorpholine] | HI |
| 25 | —N[pyrrolidine] | HI |
| 26 | —N(Me)Bz | HI |
| 27 | —N[morpholine] | fumarate |
| 28 | —N[piperazine]N—Ph | 2 HI |

EXAMPLE VI

N-(1,3-dimethyl-2-imidazolidinylidene)-N'-phenyl-1-pyrrolidinecarboximidamide fumarate Triethyloxonium fluoroborate is prepared from 1.85 g (0.020 mole) of epichlorohydrin in 7 ml of ether and 3.79 g (0.027 mole) of boron trifluoride in 3 ml of ether. The solid triethyloxonium fluoroborate is dissolved in 15 ml of dry methylene chloride and treated under nitrogen with 1,3-dimethyl-2-imidazolidine-2-one in 25 ml of methylene chloride. The reaction mixture is stirred overnight (about 16 hours) at room temperature under nitrogen. A 25 ml methylene chloride solution of N-phenyl-1-pyrrolidinecarboximidamide free base (obtained from 6.3 g, (0.020 mole) of the corresponding hydroiodide salt with 50% sodium hydroxide and dried over potassium carbonate) is added to the reaction mixture and stirred at room temperature overnight. The solvent is removed in vacuo and the oily fluoroborate salt is converted to the free base with 3 N sodium hydroxide. The organic layer is dried over potassium carbonate, filtered, evaporated in vacuo and the oil converted to the fumarate salt with one equivalent of fumaric acid (1.83 g, 0.0158 mole) in isopropanol to give 6.1 g of impure product.

Recrystallization from a 1:1 mixture of 2-propanol and ether does not purify the product. The fumarate is converted to the free base with 3 N sodium hydroxide and it is chromatographed on a dry-packed silica column (eluted with 20% of ammonia-methanol). The column is segmented into 1 inch sections and all the segments containing the pure product (as indicated by thin layer chromatography) are combined and extracted with the above solvent mixture. The solvent is then removed in vacuo at room temperature and the solid residue extracted with methanol, dried over molecular sieves (3 A), filtered over diatomaceous earth and evaporated in vacuo. The residue is taken up in chloroform, dried over potassium carbonate, filtered and evaporated to yield pure free base, N-(1,3-dimethyl-2-imidazolidinylidene)-N'-phenyl-1-pyrrolidinecarboximidamide.

Conversion to the fumarate is done with one equivalent of fumaric acid in 2-propanol. Three recrystallizations from 2-propanol-ethylacetate (1:1) gives the pure fumarate salt as a white solid, m.p. 171.5°–173.5° C.

EXAMPLE VII

The procedure of Example VI is followed, except that an equivalent amount of an appropriate guanidine derivative of formula (VII) is substituted for the one used therein, to yield as final products the following N-(1,3-dimethyl-2-imidazolidinylidene) type compounds of formula (I) in the form of the indicated acid addition (HX) salt.

| No. | $R_3$ | $-NR_1R_2$ | HX |
|---|---|---|---|
| 1 | Ph | —N⟨ ⟩S (thiazolidine) | HI |
| 2 | 4-Me—Ph | —N⟨ ⟩ (pyrrolidine) | HCl |
| 3 | 3-Cl—Ph | —N⟨ ⟩O (morpholine) | $H_3PO_4$ |
| 4 | Ph | —N(Me)⟨ ⟩S | HI |
| 5 | exo-2-norbornyl | —N⟨ ⟩ (piperidine) | HBr |
| 6 | endo-2-norbornyl | —N⟨ ⟩O (morpholine) | $MeSO_3H$ |
| 7 | 3,4-diMeO—Ph | —NEt₂ | HI |
| 8 | 1-naphthyl | —N(Me)⟨ ⟩S | fumarate |
| 9 | 1-adamantyl | —N⟨ ⟩ (pyrrolidine) | HI |
| 10 | 2,2-diphenethyl | —N⟨ ⟩ (pyrrolidine) | HCl |
| 11 | cyclopentyl | —NEt₂ | benzoate |
| 12 | tert-octyl | —N⟨ ⟩NMe (piperazine) | 2 HI |
| 13 | 4-SMe—Ph | —N⟨ ⟩O (morpholine) | HCl |
| 14 | 3-CF₃—Ph | —N(Me)⟨ ⟩S | $HNO_3$ |
| 15 | 4-NO₂—Ph | —N⟨ ⟩ (pyrrolidine) | $H_2SO_4$ |
| 16 | 4-OBz—Ph | —NEt₂ | HI |
| 17 | 4-OBz—Ph | —N⟨ ⟩ (piperidine) | HI |

EXAMPLE VIII

N-(1-methyl-1H-imidazol-2-yl)-N'-phenyl-1-pyrrolidinecarboximidamide fumarate To a chilled solution of 4.26 g (0.060 mole) of pyrrolidine in 45 ml of anhydrous ether is added dropwise under nitrogen a solution of 7.44 g (0.060 mole) of phenylisocyanide dichloride and 6.06 g (0.060 mole) of triethylamine in 45 ml of anhydrous ether. The ice bath is removed and the white suspension is stirred at room temperature for two hours. The precipitated triethylamine hydrochloride is filtered off and washed with three 30 ml portions of ether. To the combined ether filtrates is added 6.06 g (0.060 mole) of triethylamine and the mixture is again chilled in an ice-bath. A solution of 2-amino-1-methylimidazole (prepared from the corresponding hydrochloride salt with 50% sodium hydroxide and extracted with methylene chloride) in methylene chloride is added dropwise under nitrogen to the reaction mixture. The colorless solution is allowed to come to room temperature and stirred under nitrogen overnight. After evaporation of the solvent, the residue is treated with $CH_2Cl_2$ and converted to the free base form with cold 3 N sodium hydroxide. The organic layer is dried over potassium carbonate, filtered and the solvent evaporated in vacuo to give 13.8 g (95%) of an oil. Acid-base extraction gives 6.1 g (42%) of the crude free base, N-(1-methyl-1H-imidazol-2-yl)-N'-phenyl-1- pyrrolidinecarboximidamide. Recrystallization from benzene-hexane (1:1) yields pure free base, m.p. 115°–118° C., which is converted to the fumarate salt with one equivalent of fumaric acid (2.4 g, 0.002 mole) in isopropanol. Recrystallization from methanol-ether (1:1) affords 7.0 g of the pure salt, N-(1-methyl-1H-imidazol-2-yl)-N'-phenyl-1-pyrrolidinecarboximidamide fumarate, m.p. 156.5°–159.5° C.

EXAMPLE IX

By following the procedure of Example XIII, except that an equivalent amount of an appropriate isocyanide dichloride of formula (XII) is used as the reactant with 2-amino-1-methylimidazole, the following N-(1-methyl-1H-imidazol-2-yl) type products of formula (I) are obtained either as the free base or as the indicated acid addition (HX) salt form.

| No. | R₃ | —NR₁R₂ | HX |
|---|---|---|---|
| 1 | 2-Br-4-Me—Ph | —N(piperidinyl) | — |
| 2 | cyclohexyl | —N(thiomorpholinyl) | HCl |
| 3 | 4-Me—Ph | —N(Me)(thianyl) | HCl |
| 4 | 4-Cl-2,6-diEt—Ph | —N(morpholinyl) | — |
| 5 | 3-Cl-4-OMe—Ph | —N(thiomorpholinyl) | — |
| 6 | 3-F—Ph | —N(Me)(thianyl) | HNO₃ |
| 7 | 3-CF₃—Ph | —N(morpholinyl) | — |
| 8 | 1-naphthyl | —N(pyrrolidinyl) | fumarate |
| 9 | Ph | —N(piperidinyl) | fumarate |
| 10 | cyclohexyl | —N(NPh-piperazinyl) | — |
| 11 | Bz | —N(pyrrolidinyl) | — |
| 12 | Ph | —NEt₂ | HCl |
| 13 | 4-OBz—Ph | —N(morpholinyl) | — |

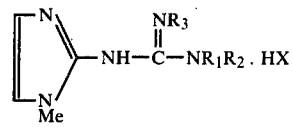

| No. | R₃ | —NR₁R₂ | HX |
|---|---|---|---|
| 14 | 4-OBz—Ph | —N(Me)(thianyl) | — |

EXAMPLE X

N-(1-methylimidazol-2-yl)-N'-phenylthiourea

A 4.8 g (0.036 mole) sample of 2-amino-1-methylimidazole hydrochloride is suspended in 20 ml of methylene chloride and stirred with 10 ml of 50% NaOH. The organic layer is separated and the aqueous layer is extracted twice with 20 ml portions of fresh methylene chloride. The combined organic extracts are dried over K₂CO₃ and filtered. The filtrate is treated with 4.86 g (0.036 mole) of phenyl isothiocyanate. The solution is heated under reflux for 4 hr. Evaporation of the solvent in vacuo followed by recrystallization of the residue from acetone-ether (1:1) and MeOH-ether (1:1) gives the product, N-(1-methylimidazol-2-yl)-N'-phenylthiourea; m.p. 170°–172° C.

EXAMPLE XI

Methyl N-(1-methylimidazol-2-yl)-N'-phenylcarbamimidothioate hydroiodide

A solution of 3.0 g (0.013 mole) of N-(1-methylimidazol-2-yl)-N'-phenylthiourea in 50 ml of methanol is added 2.13 g (0.015 mole) of methyl iodide. The solution is heated under reflux for 2 hr, the solvent is evaporated and the residue is recrystallized from acetone-ether to give methyl N-(1-methylimidazol-2-yl)-N'-phenylcarbamimidothioate hydroiodide; m.p. 115°–118° C.

EXAMPLE XII

By following the procedure of Example X, except that an equivalent amount of an appropriate isothiocyanate is employed instead of the phenyl isothiocyanate used therein, and by then utilizing an equivalent amount of the thus-obtained thiourea as the precursor to be S-methylated according to the procedure of Example XI, the following pseudothioureas of formula (V) are obtained.

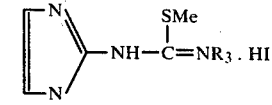

| No. | R₃ | No. | R₃ |
|---|---|---|---|
| 1 | 2,4-diF—Ph | 8 | 4-Cl—Ph |
| 2 | 4-CF₃—Ph | 9 | 3,5-diOMe—Ph |
| 3 | 2,4,5-triCl—Ph | 10 | 3-OBz—Ph |
| 4 | 5-Cl-2-OMe—Ph | 11 | 2,4-diMe—Ph |
| 5 | 4-Br—Ph | 12 | 3-NO₂—Ph |
| 6 | 4-Br-3-Cl—Ph | 13 | 2-OMe-5-Me—Ph |
| 7 | 4-OEt—Ph | 14 | 3,4-diCl—Ph |

| | SMe |
|---|---|
| ![structure: 1-methylimidazol-2-yl-NH-C(SMe)=NR₃ · HI] | |

| No. | R₃ | No. | R₃ |
|---|---|---|---|
| | | 15 | 4-OBz—Ph |

EXAMPLE XIII

N-(1-methylimidazol-2-yl)-N'-phenyl-4-morpholinecarboximidamide hydrochloride

A solution of 1.5 g (0.004 mole) of methyl N-(1-methylimidazol-2-yl)-N'-phenylcarbamimidothioate hydroiodide and 0.73 g (0.0084 mole) of morpholine in 30 ml of t-BuOH is refluxed overnight. Upon cooling, ether is added and morpholine hydroiodide is removed by filtration. The filtrate is taken to dryness and the residue is taken up in CH₂Cl₂ and converted to the free base with 3 N NaOH. The organic layer is separated, dried over K₂CO₃, filtered and the solvent is removed in vacuo to give a residue of N-(1-methylimidazol-2-yl)-N'-phenyl-4-morpholine carboximidamide, which is taken up in acetone and converted to the hydrochloride salt with ethereal HCl.

EXAMPLE XIV

The procedure of Example XIII is followed except that an equivalent amount of each pseudothiourea obtained in Example XII is reacted with an equivalent amount of an appropriate amine of the formula HNR₁R₂ to yield the following products of formula (I).

[structure: 1-methylimidazol-2-yl-NH-C(NR₃)=NR₁R₂ · HCl]

| No. | R₃ | —NR₁R₂ |
|---|---|---|
| 1 | 2,4-diF—Ph | —N(pyrrolidine) |
| 2 | 4-CF₃—PH | —N(thiomorpholine) |
| 3 | 2,4,5-triCl—Ph | —N(Me)(thiazolidine) |
| 4 | 5-Cl-2-OMe—Ph | —N(piperidine) |
| 5 | 4-Br—Ph | —N(Me)(piperidine) |
| 6 | 4-Br-3-Cl—Ph | —NEt₂ |
| 7 | 4-OEt—Ph | —N(morpholine) |
| 8 | 4-Cl—Ph | —N(pyrrolidine) |
| 9 | 3,5-diOMe—Ph | —N(thiomorpholine) |
| 10 | 3-OBz—Ph | —N(Me)Bz |
| 11 | 2,4-diMe—Ph | —N(morpholine) |
| 12 | 3-NO₂—Ph | —N(piperidine) |
| 13 | 2-OMe-5-Me—Ph | —N(Me)Et |
| 14 | 3,4-diCl—Ph | —N(pyrrolidine) |
| 15 | 4-OBz—Ph | —N(pyrrolidine) |

EXAMPLE XV

N-(1-adamantyl)-N'-(1-methylimidazol-2-yl)-1-pyrrolidinecarboximidamide

To 18.85 g (0.1 mole) of dichloromethylenetetramethylene ammonium chloride in 100 ml of dry methylene chloride is added dropwise a solution of 15.13 g (0.1 mole) of 1-adamantylamine and 20.2 g (0.2 mole) of triethylamine in dry CH₂Cl₂ with cooling (ice bath) under dry N₂. After the addition is complete, the mixture is stirred at room temperature for 3 hrs. Then a dry methylene chloride solution containing 9.71 g (0.1 mole) of 2-amino-1-methylimidazole and 10.1 g (0.1 mole) of triethylamine is added dropwise over 1 hr with cooling. After the addition the mixture is stirred under dry N₂ overnight at room temperature. The mixture is then shaken with excess 3 N NaOH and the organic layer is separated, dried (K₂CO₃), filtered and the solvent and residual triethylamine is removed in vacuo giving N-(1-adamantyl)-N'-(1-methylimidazol-2-yl)-1-pyrrolidinecarboximidamide free base.

EXAMPLE XVI

By repeating the procedure of Example XV but substituting for dichloromethylenetetramethyleneammonium chloride an appropriate dichloromethyleneammonium salt and an appropriate R₃NH₂ amine for 1-adamantylamine, the following N-(1-methylimidazol-2-yl)-N'-substituted-1-(or 4) carboximidamides are obtained. Treatment with appropriate acid (HX) affords the indicated acid addition salt.

| | NR₃ ⫽ —NH—C—NR₁R₂ . HX | | |
|---|---|---|---|
| No. | R₃ | —NR₁R₂ | HX |
| 1 | cyclohexyl | 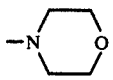 | HI |
| 2 | α,α-diMe-phenethyl | —NEt₂ | HO₃SMe |
| 3 | d,1-α-Me—Bz | —NMe₂ | HCl |
| 4 | exo-2-norbornyl | 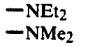 | — |
| 5 | benzhydryl | 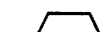 | — |
| 6 | 2,2-diphenylethyl |  | p-TsOH |
| 7 | 3,4-diOMe—Ph | —N(Me)Bz | — |
| 8 | Bz | —N(IsoPr)₂ | H₂SO₄ |
| 9 | 3-Cl—Ph | | H₃PO₄ |
| 10 | 2,4-diMe—Ph |  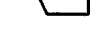 | L(+)-tartrate |
| 11 | 1,2-diphenylethyl | —NMe₂ | — |
| 12 | 4-OBz—Ph |  | HCl |
| 13 | neopentyl | 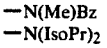 | — |
| 14 | tert-octyl |  | — |

EXAMPLE XVII

N-(4,5-dihydro-1-methylimidazol-2-yl)-N'-(4-hydroxyphenyl)-1-pyrrolidinecarboximidamide hydroiodide To a solution of 37.8 g (0.1 mole) of N-(4-benzyloxyphenyl)-N'-4,5-dihydro-1-methylimidazol-2-yl-1-pyrrolidinecarboximidamide in 150 ml of glacial acetic acid in a 500 ml hydrogenation bottle, is added 0.5 g of 30% Pd/C catalyst. The mixture is hydrogenated at a starting pressure of 60 p.s.i. for 4 hr, then filtered from catalyst and the acetic acid removed in vacuo. The residue is taken up in tert-butanol and treated with a stoichiometric amount of 48% HI. Ether is added causing N-(4,5-dihydro-1-methylimidazol-2-yl)-N'-(4-hydroxyphenyl)-1-pyrrolidinecarboximidamide hydroiodide to precipitate.

EXAMPLE XVIII

The debenzylation procedure of Example XVII is followed, escept that an equivalent amount of an appropriate R₃=benzyloxyphenyl precursor is initially employed, to yield the following R₃=hydroxyphenyl derivatives of formula (I) in the form of the hydroiodide salt.

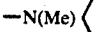

| Z | —NR₁R₂ |
|---|---|
|  | —NEt₂ |
| " | 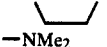 |
| 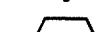 | 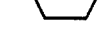 |
| " | 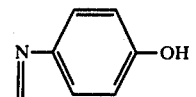 |
| | —N(Me)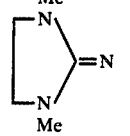 |
| 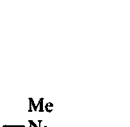 | 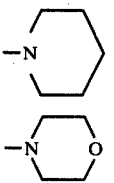 |

EXAMPLE XIX

2-Imino-1,3-dimethylimidazolidine sulfate (2:1 salt)

Triethyloxonium tetrafluoroborate is prepared in ether on a 1.2 mole scale from 327.1 g (1.6 mole) of boron trifluoride etherate and 111.0 g (1.2 mole) of epichlorohydrin under dry N₂. The resulting crystals are washed with fresh anhydrous ether by decantation (2×250 ml). The resulting crystals of triethyloxonium tetrafluoroborate are dissolved in 1 liter of dry methylene chloride. To this solution is added 114 g (1 mole) of 1,3-dimethylimidazolidine-2-one. The mixture is allowed to stir at ambient temperatures for 3 hrs. Then ahydrous NH₃ is added vigorously for 10 min. The mixture becomes warm. Ammonia addition is continued at a gentle rate for 20 min more and then allowed to stir for 0.5 hr. The mixture is filtered from inorganic material, concentrated to a volume of 200 ml and let stand overnight. Treatment with 100 ml of 50% NaOH with cooling (ice-water) and shaking converts the product to free base. The aqueous layer is washed with fresh CH₂Cl₂ (3×100 ml). The combined, dried (K₂CO₃) organic layers are filtered (diatomaceous earth) giving a cloudy filtrate. Removal of solvent in vacuo with gentle heat causes separation of more solid. To the oily suspension is added 200 ml ether and the solution is refiltered. The filtrate is reduced to a volume of about 100 ml and then taken up in MeOH (200 ml). The resulting solution is cooled while concentrated H₂SO₄ is added until pH 6. Boiling on a stirring hot place with addition of 2-PrOH to replace lost MeOH gives a crop of solid which separates from the hot solution. The crystals are filtered and the filtrate is concentrated with more 2-PrOH added until MeOH is removed. Cooling affords a second crop coated by a syrup. The gummy crystals are washed with fresh 2-PrOH and combined with the first crop. The combined crops are recrystallized by dissolving in MeOH, filtering (diatomaceous earth), adding 2-PrOH and concentrating as before to give pure 2-imino-1,3-dimethylimidazolidine ½ sulfate; m.p. >300° C. A second crop is obtained from the mother liquors; m.p. 300° C. Yield 69.5 g total (42.8%).

EXAMPLE XX

N-(4-Hydroxyphenyl)-N'-(1-methylimidazol-2-yl)-4-thiamorpholinecarboximidamide hydroiodide A 50 ml round-bottomed flask is charged with 3.75 g (0.007 mole) of N-(4-benzyloxyphenyl-N'-(1-methylimidazol-2-yl)-4-thiamorpholinecarboximidamide hydroiodide (Ex. V-12) 5.9 g (0.021 mole) of 50% hydriodic acid, and 6.0 g (0.1 mole) of glacial acetic acid. The mixture is heated under reflux for 6 hr, then the excess HI and solvent are removed under reduced pressure leaving as the residue, N-(4-hydroxyphenyl)-N'-(1-methylimidazol-2-yl)-4-thiamorpholinecarboximidamide hydroiodide.

What is claimed is:

1. A diaza heterocyclic derivative of guanidine selected from the group consisting of a compound having the formula:

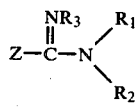

and the pharmaceutically acceptable acid addition salts thereof wherein:

Z is a member selected from the group consisting of:

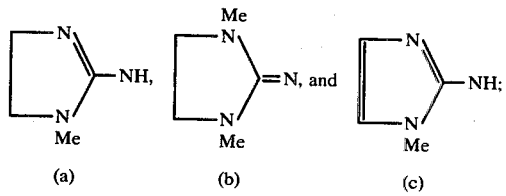

$R_1$ is a member selected from the group consisting of methyl and ethyl;

$R_2$ is a member selected from the group consisting of loweralkyl, cyclopentyl, cyclohexyl and benzyl;

taken together represents a member selected from group consisting of:

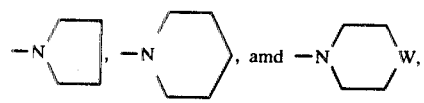

wherein W is a member selected from the group consisting of O, S, N-loweralkyl and N-phenyl; and $R_3$ is a member selected from the group consisting of alkyl having from 4 to 10 carbons;
phenyl; methylenedioxyphenyl; phenyl substituted with from 1 to 3 substituents each selected from the group consisting of halo, loweralkyl and loweralkoxy; and phenyl substituted with a member selected from the group consisting of hydroxy, benzyloxy, nitro; trifluoromethyl and methylthio;
naphthyl; cyclopentyl; cyclohexyl; exo-2-norbornyl; endo-2-norbornyl; 1-adamantyl;
arylalkyl in which the aryl function is phenyl and the alkyl function has from 1 to 4 carbons; and
diphenylalkyl in which the alkyl function has from to 2 carbons.

2. A compound selected from the group consisting of N-(1-methyl-2-imidazolidinylidene)-N'-phenyl-1-pyrrolidinecarboximidamide and the pharmaceutically acceptable acid addition salts thereof.

3. A compound selected from the group consisting of N-(1,3-dimethyl-2-imidazolidinylidene)-N'-phenyl-1-pyrrolidinecarboximidamide and the pharmaceutically acceptable acid addition salts thereof.

4. A compound selected from the group consisting of N-(1-methyl-1H-imidazol-2-yl)-N'-phenyl-1-pyrrolidinecarboximidamide and the pharmaceutically acceptable acid addition salts thereof.

5. A compound selected from the group consisting of N-(1-methylimidazol-2-yl)-N'-phenyl-4-morpholinecarboximidamide and the pharmaceutically acceptable acid addition salts thereof.

6. A compound selected from the group consisting of N-(1-adamantyl)-N'-(1-methylimidazol-2-yl)-1-pyrrolidinecarboximidamide and the pharmaceutically acceptable acid addition salts thereof.

7. A compound selected from the group consisting of N-(4,5-dihydro-1-methylimidazol-2-yl)-N'-(4-hydroxyphenyl)-1-pyrrolidinecarboximidamide and the pharmaceutically acceptable acid addition salts thereof.

8. A compound selected from the group consisting of N-(4-hydroxyphenyl)-N'-(1-methylimidazol-2-yl)-4-thiamorpholinecarboximidamide and the pharmaceutically acceptable acid addition salts thereof.

* * * * *